United States Patent [19]

Beaulieu et al.

[11] Patent Number: 5,545,640
[45] Date of Patent: Aug. 13, 1996

[54] PROTEASE INHIBITING SUCCINIC ACID DERIVATIVES

[75] Inventors: Pierre L. Beaulieu, Rosemère; Ingrid Guse, Kirkland, both of Canada

[73] Assignee: Bio-Mega/Boehringer Ingeleheim Research Inc., Laval, Canada

[21] Appl. No.: 416,239

[22] Filed: Apr. 4, 1995

[51] Int. Cl.$^6$ .................. C07D 215/48; C07C 271/20; A61K 31/47
[52] U.S. Cl. .............. 514/311; 514/307; 514/419; 514/485; 514/542; 544/355; 546/146; 546/169; 548/492; 560/32; 560/39; 564/56; 564/153
[58] Field of Search ............... 546/169, 146; 560/32, 39; 564/153, 56; 514/311, 307, 485, 419, 542; 544/355

[56] References Cited

FOREIGN PATENT DOCUMENTS

| | | |
|---|---|---|
| 375451 | 6/1990 | European Pat. Off. . |
| 411751 | 2/1991 | European Pat. Off. . |
| 416740 | 3/1991 | European Pat. Off. . |

Primary Examiner—Bernard Dentz
Attorney, Agent, or Firm—R. P. Raymond; M-E. M. Devlin; A. R. Stempel

[57] ABSTRACT

Disclosed herein are compounds which inhibit human immunodeficiency virus (HIV) protease activity and inhibit HIV replication in human cells. Thus, the compounds are indicated for the treatment of HIV infections. The compounds can be represented by the formula

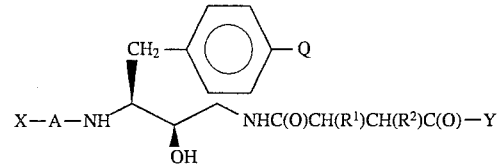

wherein X is a terminal group, for example, an aryloxycarbonyl, an alkanoyl or an arylalkyl carbamoyl; A is absent or an amino acid or a derived amino acid; either $R^1$ or $R^2$ is hydrogen while the other is alkyl or $R^1$ and $R^2$ are joined to form a cyclohexane; Q is hydrogen, hydroxy, halo or lower alkoxy; and Y is a terminal group, for example, an alkylamino, alkoxy or an optionally substituted anilino.

10 Claims, No Drawings

PROTEASE INHIBITING SUCCINIC ACID DERIVATIVES

FIELD OF INVENTION

This invention relates to compounds exhibiting activity against particular retroviruses, to processes for producing the compounds, to pharmaceutical preparations thereof, and to a method of using the compounds to combat infections caused by the retroviruses.

BACKGROUND OF THE INVENTION

In 1983, a retrovirus, known as human immunodeficiency virus type 1 (HIV-1), was established as a causative agent of acquired immune deficiency syndrome (AIDS), see R. C. Gallo and L. Montagnier, Scientific American, 259 (4), 40 (1988). This virus has become a pestilence of alarming proportion. More recently, the closely related virus, human immunodeficiency virus type 2 (HIV-2) has been identified as a second causative agent of AIDS.

The identification of human immunodeficiency virus (HIV) as a causative agent and the development of methods to grow the virus in quantity have resulted in the discovery of compounds which inhibit the replication of HIV in vitro. The most important class of inhibitor compounds identified in this manner is a group of dideoxynucleosides of which 3'-azido-3'-deoxythymidine (known also as zidovudine or AZT) and, more recently, 2',3'-dideoxyinosine (known also as didanosine or DDI) are used therapeutically to manage certain patients with symptomatic HIV infections. This class of compounds has been found to interfere with the life cycle of HIV by inhibiting reverse transcriptase. This enzyme converts viral RNA to double-stranded deoxyribonucleic acid (DNA) and as such is an essential enzyme for HIV replication. In addition to inhibiting reverse transcriptase, other stages of the HIV life cycle have been identified as targets for developing anti-AIDS drugs. One target that is receiving increased attention is an HIV-encoded enzyme known as HIV protease. This enzyme, like the reverse transcriptase, is encoded by the pol gene and is essential for HIV growth. It is responsible for effecting certain cleavages within the gag (p55) or gag-pol (p160) proteins to release structural proteins, e.g. p17 and p24, and enzymes, including itself, found in mature infectious virions. Thus, inhibitors of HIV protease can block the HIV life cycle.

The increased attention given to HIV protease over the last few years is reflected in the increase in reports of the discovery of agents which block the enzyme. See, for example, the recent review on HIV protease inhibitors by S. Thaisrivongs, Annual Reports In Medicinal Chemistry, 29, 133 (1994). As noted in the latter review several potent series of HIV protease inhibitors have been realized by the placement of a hydroxyethylamine transition state analog (TSA) in a peptide having the p17/p24 substrate cleavage site sequence.

The present application discloses succinic acid derivatives having an hydroxyethylamine TSA incorporated therein. The derivatives are potent inhibitors of HIV protease. Moreover, a capacity to inhibit HIV induced cytopathogenic effects in human cells has been demonstrated for the compounds. Such properties, together with the attributes of a relatively selective action and an apparent lack of toxicity, render the compounds useful as agents for combating HIV infections.

The combination of a succinyl moiety with a hydroxyethylamine TSA in the structure of an HIV protease inhibitor appears to be unique, although this structural feature could be constructed from the broadest disclosure of certain patent applications relating to renin inhibitors and antiretroviral agents, such as:

P. Ham and S. A. Smith, European patent application 375 451, published Jun. 27, 1990, S. A. Smith and P. Ham, Australian patent application 9056256, published Dec. 13, 1990, and S. A. Smith et al., European patent application 416 740, published Mar. 13, 1991.

SUMMARY OF THE INVENTION

Reference can be made to the "Details of the Invention" section, hereinafter, for explanations of some of the less common terms and symbols used to describe the invention.

The compounds of this invention are represented by formula 1:

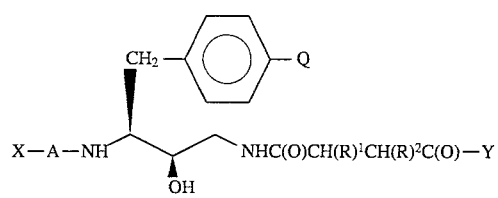

wherein X is $R^3OC(O)$, $R^3C(O)$ or $R^3NHC(O)$ wherein $R^3$ is (i) lower alkyl,
(ii) lower cycloalkyl,
(iii) phenyl; phenyl monosubstituted with halo, hydroxy, amino, lower alkyl or lower alkoxy; or phenyl disubstituted or trisubstituted with the same or different substituent selected from the group consisting of halo, amino and lower alkyl;
(iv) phenyl(lower)alkyl or phenyl(lower)alkyl wherein the aromatic portion thereof is monosubstituted with halo, hydroxy, lower alkyl or lower alkoxy,
(v) phenyl(lower)alkenyl,
(vi) 1-naphthyl or 2-naphthyl,
(vii) Het or Het-(lower alkyl) wherein Het represents a five- or six-membered monocyclic, or a nine- or ten-membered bicyclic, radical containing one or two heteroatoms selected from nitrogen, oxygen and sulfur, the heterocyclic radical being either unsubstituted or having one or two of the same or different substituents selected from the group consisting of halo, hydroxy, amino, lower alkyl or lower alkoxy; or X is $R^{3A}NHCH_2C(O)$ wherein $R^{3A}$ is lower alkyl or phenyl, or X is $R^{3B}OCH_2C(O)$ wherein $R^{3B}$ is phenyl, phenyl monosubstituted with halo or lower alkyl, or phenyl disubstituted or trisubstituted with the same or different substituent selected from the group of halo and lower alkyl;

A is absent or the divalent radical $NR^4CHR^5C(O)$ wherein $R^4$ is hydrogen or lower alkyl and $R^5$ is lower alkyl, 1-carboxycyclobut-1-yl, 1-carboxycyclopent-1-yl, or lower alkyl monosubtituted with carboxy, carbamyl, (lower alkoxy)carbonyl, benzyloxycarbonyl, hydroxy, cyano or benzyloxy;

$R^1$ is lower alkyl and $R^2$ is hydrogen, or $R^1$ is hydrogen and $R^2$ is lower alkyl, or $R^1$ and $R^2$ together with the carbon atoms to which they are attached form a 1,2-cyclohexanediyl;

Q is hydrogen, hydroxy, halo or lower alkoxy; and

Y is (1–8C)alkylamino, (1–8C)alkoxy, phenylamino or phenylamino having one or two of the same or different substituents on the phenyl portion thereof selected from the group consisting of lower alkyl, lower alkoxy, hydroxy, halo, amino or lower alkylamino; or a therapeutically acceptable acid addition salt thereof.

A preferred group of compounds of this application is represented by formula 1 wherein X is (i) $R^3OC(O)$ wherein $R^3$ is lower alkyl, lower cycloalkyl, phenyl, phenyl(lower alkyl) or phenyl(lower)alkyl wherein position 4 of the phenyl portion is substituted with halo, lower alkyl or lower alkoxy;

(ii) $R^3C(O)$ wherein $R^3$ is lower alkyl; lower cycloalkyl; phenyl; phenyl monosubstituted with halo, hydroxy, lower alkyl or lower alkoxy; phenyl disubstituted or trisubstituted with the same or different substituent selected from the group consisting of chloro, fluoro, amino or methyl; phenyl(lower)alkyl; phenyl(lower)alkyl monosubstituted at position 4 of the phenyl portion with halo, hydroxy, lower alkyl or lower alkoxy; phenyl(lower)alkenyl; 1-naphthyl; 2-naphthyl; Het, Het-$CH_2$ or Het-$CH_2CH_2$ wherein Het is as defined hereinabove; or (phenylamino)methyl; or (iii) $R^3NHC(O)$ wherein $R^3$ is lower alkyl; lower cycloalkyl; phenyl; phenyl monosubstituted with halo, lower alkyl or lower alkoxy; benzyl or benzyl monosubstituted at position 4 of the phenyl portion with halo, lower alkyl or lower alkoxy; or X is $R^{3A}NHCH_2C(O)$ wherein $R^{3A}$ is lower alkyl or phenyl, or X is $R^{3B}OCH_2C(O)$ wherein $R^{3B}$ is phenyl or phenyl mono-, di- or trisubstituted with lower alkyl or halo at a position or positions selected from the group consisting of positions 2, 4 and 6;

A is absent or the divalent radical $NR^4CHR^5C(O)$ wherein $R^4$ is hydrogen or methyl and $R^5$ is as defined hereinabove;

$R^1$ is 1-methylethyl, 1,1-dimethylethyl, 1,1-dimethylpropyl, 2,2,-dimethylpropyl, 3-methylbutyl, 3,3-dimethylbutyl, 4-methylpentyl, 4,4-dimethylpentyl and $R^2$ is hydrogen, or $R^1$ is hydrogen and $R^2$ is 1-methylethyl, 1,1-dimethylethyl, 1,1-dimethylpropyl, 2,2-dimethylpropyl, 3-methylbutyl, 3,3-dimethylbutyl, 4-methylpentyl or 4,4-dimethylpentyl, or $R^1$ and $R^2$ together with the carbon atoms to which they are attached form a 1,2-cyclohexanediyl; and Q and Y are as defined hereinbefore; or a therapeutically acceptable acid addition salt thereof.

A more preferred group of compounds are represented by formula 1 wherein X is (i) $R^3OC(O)$ wherein $R^3$ is isopropyl, tert-butyl, benzyl or 2-phenylethyl; (ii) $R^3C(O)$ wherein $R^3$ is methyl, ethyl, propyl, cyclopropyl, cyclohexyl, phenyl, 4-chlorophenyl, 2-fluorophenyl, 2,4-dichlorophenyl, 2,6-dichlorophenyl, 2,3,6-trichlorophenyl, 2-methylphenyl, 4-methylphenyl, 2,4-dimethylphenyl, 2,5-dimethylphenyl, 2,6-dimethylphenyl, 3-amino-2-methylphenyl, benzyl, (4-fluorophenyl)methyl, (4-methoxyphenyl)methyl, 2-phenylethyl, 3-phenylpropyl, 4-phenylbutyl, 5-phenylpentyl, 2-(4-fluorophenyl)ethyl, 2-(4-hydroxyphenyl)butyl, (4-methylphenyl)butyl, 3-(4-methoxyphenyl)propyl, 1-oxo-3-phenyl-2-propenyl, 1-naphthyl, 2-naphthyl, 2-furyl, 2-thienyl, 2-pyridinyl, 4-pyridinyl, 4-thiazolyl, 4-isoxazolyl, 2-quinolyl, 3-quinolyl, 4-quinolyl, 6-quinolyl, 8-quinolyl, 4-methoxy-2-quinolyl, 1-isoquinolyl, 3-isoquinolyl, 2-quinoxalinyl, 1-methyl-2-indolyl, 2,3-dihydroindol-2(R or S)-yl, 1,2,3,4-tetrahydroisoquinol-3(R or S)-yl, 2-pyridinyl-methyl, 2-morpholinoethyl, 2-piperidinoethyl, 3-(4-thiazolyl)propyl, or (phenylamino)methyl; (iii) $R^3NHC(O)$ wherein $R^3$ is lower alkyl, benzyl or benzyl monosubstituted on the aromatic portion thereof with fluoro, methyl or methoxy; or X is $R^{3A}NHCH_2C(O)$ wherein $R^{3A}$ is methyl or phenyl, or X is $R^{3B}OCH_2C(O)$ wherein $R^{3B}$ is phenyl, 2-methylphenyl, 2,4-dimethylphenyl, 2,6-dimethylphenyl, 2,4,6-trimethylphenyl, 4-chlorophenyl or 4-fluorophenyl;

A is absent or $NR^4CHR^5C(O)$ wherein $R^4$ is hydrogen or methyl and $R^5$ is 1-methylethyl, 1,1-dimethylethyl, 1-methylpropyl, 2-methylpropyl, 1-carboxycyclopent 1-yl, $CH_2C(O)OH$, (R)—$CH(CH_3)C(O)OH$, $CH_2CH_2C(O)OH$, $CH_2C(O)NH_2$, $CH_2CH_2C(O)NH_2$, $CH_2C(O)OMe$, (R)—$CH(CH_3)C(O)OBzl$, $CH_2OH$, $CH(OH)CH_3$ or $CH_2CN$;

$R^1$ is 1,1-dimethylethyl, 2,2-dimethylpropyl, 1-methylbutyl, 3,3-dimethylbutyl or 4,4-dimethylpentyl and $R^2$ is hydrogen, or $R^1$ is hydrogen and $R^2$ is tert-butyl, 2,2-dimethylpropyl, 1-methylbutyl, 3,3-dimethylbutyl or 4,4-dimethylpentyl; Q is hydrogen, hydroxy or methoxy; and Y is isopropylamino, tert-butylamino, 1-methylpropylamino, 2-methylpropylamino, 1-ethylpropylamino, 1-isopropyl-2-methylpropylamino, 1-ethylbutylamino, 1-propylbutylamino, isopropoxy, 1-ethylpropoxy, phenylamino or phenylamino having one or two of the same or different substituents selected from the group consisting of methyl, ethyl, propyl, isopropyl, hydroxy, fluoro or chloro; or a therapeutically acceptable acid addition salt thereof.

A most preferred group is represented by formula 1 wherein X is tert-butoxycarbonyl, benzyloxycarbonyl, (2-phenylethoxy)carbonyl, acetyl, benzoyl, (2,4-dichlorophenyl) carbonyl, (2,3,6-trichlorophenyl)carbonyl, (2-methylphenyl)carbonyl, (2,5-dimethylphenyl)carbonyl, (2,6-dimethylphenyl)carbonyl, (3-amino-2-methylphenyl)carbonyl, phenoxymethylcarbonyl, 2-quinolylcarbonyl, 3-quinolylcarbonyl, 4-quinolylcarbonyl, 6-quinolylcarbonyl, 8-quinolylcarbonyl, 4-methoxy-2-quinolylcarbonyl, 1-isoquinolylcarbonyl, 3-isoquinolylcarbonyl, 2-quinoxalinylcarbonyl, 1-methyl-2-indolylcarbonyl, 2,3-dihydroindol-2(R or S)-ylcarbonyl, 1,2,3,4-tetrahydroisoquinol-3(R or S)-ylcarbonyl, 1-oxo-3-piperidinopropyl, (phenylamino)methylcarbonyl or (benzylamino)carbonyl; A is Val, N-MeVal, Tbg, Ile, Leu, Asp(cyPn), Asp, βMeAsp, Glu, Asn, Gln, βMeASp(OBzl), Ser, Thr or βCN-Ala; $R^1$ is 1,1-dimethylethyl; $R^2$ is hydrogen; Q is hydrogen or hydroxy; Y is 1-ethylpropylamino, 1-isopropyl-2-methylpropylamino, 1-propylbutylamino, isopropoxy, 1-ethylpropoxy, phenylamino, (2,6-dimethylphenyl)amino, (2,6-diethylphenyl)amino or (2,6-diisopropylphenyl)amino; and the asymmetric carbon atom bearing $R^1$ has the (R) configuration.

Another most preferred group of compounds is represented by formula 1 wherein X is (2-methylphenoxy)acetyl, (2,4-dimethylphenoxy)acetyl, (2,6-dimethylphenoxy)acetyl or (2,4,6-trimethylphenoxy)acetyl, A is absent, $R^1$ is 1,1-dimethylethyl, $R^2$ is hydrogen, Q is hydrogen or hydroxy, and Y is as defined in the last instance; and the asymmetric carbon atom bearing $R^1$ has the (R) configuration.

A more specific group of preferred compounds are represented by formula 1 wherein X is benzyloxycarbonyl, 2-quinolylcarbonyl or 2-quinoxalinylcarbonyl, A is Val, Tbg, Asn or Thr, $R^1$ is 1,1-dimethylethyl, $R^2$ is hydrogen, Q is hydrogen or hydroxy, Y is 1-ethylpropylamino or (2,6-dimethylphenyl)amino, and the asymmetric carbon atom bearing $R^1$ has the (R) configuration.

Preferably, with reference to the compound of formula 1 in which A is the radical $NR^4CHR^5C(O)$, the asymmetric carbon atom bearing $R^5$ has the (S) configuration.

Included within the scope of this invention is a pharmaceutical composition for treating HIV infections in a human comprising a compound of formula 1, or a therapeutically acceptable acid addition salt thereof, and a pharmaceutically acceptable carrier.

The scope of the invention includes as well a method for treating HIV infections in a human comprising administering thereto an effective amount of the compound of formula 1, or a therapeutically acceptable acid addition salt thereof.

Also included within the scope is a method for protecting human cells against HIV pathogenesis comprising treating said cells with an anti-HIV effective amount of a compound of formula 1, or a therapeutically acceptable acid addition salt thereof.

Processes for preparing the compounds of formula 1 are described hereinafter.

Details of the Invention

GENERAL

In general, the abbreviations used herein for designating the amino acids and the protective groups are based on recommendations of the IUPAC-IUB Commission of Biochemical Nomenclature, see European Journal of Biochemistry 138, 9 (1984). For instance, Val, Ile, Leu, Asp, Glu, Asn, Gln, Ser and Thr represent the residues of L-valine, L-isoleucine, L-leucine, L-aspartic acid, L-glutamic acid, L-asparagine, L-glutamine, L-serine and L-threonine, respectively.

The term "residue" with reference to an amino acid means a radical derived from the corresponding α-amino acid by eliminating the hydroxyl of the carboxy group and one hydrogen of the α-amino group.

The term "lower alkyl" as used herein, either alone or in combination with a radical, means straight chain alkyl radicals containing one to six carbon atoms and branched chain alkyl radicals containing three to six carbon atoms and includes methyl, ethyl, propyl, butyl, hexyl, 1-methylethyl, 1-methylpropyl, 2-methylpropyl, 1-ethylpropyl and 1,1-dimethyl-ethyl (also known as tert-butyl).

The term "lower cycloalkyl" as used herein, either alone or in combination with a radical, means saturated cyclic hydrocarbon radical containing from three to six carbon atoms and includes cyclopropyl, cyclobutyl, cyclopentyl and cyclohexyl.

The term "lower alkoxy" as used herein means straight chain alkoxy radical containing one to six carbon atoms and branched chain alkoxy radicals containing three to four carbon atoms and includes methoxy, ethoxy, propoxy, hexoxy, 1-methylethoxy, butoxy and 1,1-dimethylethoxy. The latter radical is known commonly as tert-butyloxy. The term "(1–8C)alkoxy" means alkoxy radicals containing one to eight carbon atoms and includes, for example, methoxy, propoxy, isopropoxy, 1-ethylpropoxy and 1-propylbutoxy.

The term "amino" as used herein means an amino radical of formula —NH$_2$. The term "lower alkylamino" as used herein means alkylamino radicals containing one to six carbon atoms and includes methylamino, ethylamino, propylamino, 1-methylethylamino and 2-methylbutylamino. The term "(1–8C)alkylamino" as used herein means alkylamino radicals containing one to eight carbon atoms and includes, for example, methylamino, propylamino, 1-ethylpropylamino and 1-propylbutylamino.

The term "halo" as used herein means a halo radical selected from bromo, chloro, fluoro or iodo.

The term "1,2-cyclohexandiyl" means a divalent cyclohexane radical derived by the removal of two hydrogen atoms, each from adjoining carbon atoms, of the radical. In the present instance, the two carbon atoms are those bearing R$^1$ and R$^2$.

The term "Het" as used herein means a monovalent radical derived by removal of a hydrogen atom from a five- or six-membered monocyclic, or a nine- or ten-membered bicyclic, saturated or unsaturated heterocycle containing from one to two heteroatoms selected from nitrogen, oxygen and sulfur. Optionally, the heterocycle may bear one or two substituents; for example, lower alkyl, lower alkoxy, halo, amino or lower alkylamino. Examples of suitable heterocycles and optionally substituted heterocycles include pyrrolidine, tetrahydrofuran, thiazolidine, pyrrole, 1H-imidazole, 1-methyl-1H-imidazole, pyrazole, furan, thiophene, oxazole, isoxazole, thiazole, 2-methylthiazole, 2-aminothiazole, 2-(methylamino)thiazole, piperidine, 1,4-dioxane, 4-morpholine, pyridine, pyrimidine, 2,4-dimethylpyrimidine, indole, 1-methylindole, 2,3-dihydroindole, quinoline, 4-methoxyquinoline, isoquinoline, quinoxaline and 1,2,3,4-tetrahydroisoquinoline.

The term "pharmaceutically acceptable carrier" as used herein means a non-toxic, generally inert vehicle for the active ingredient, which does not adversely affect the ingredient.

The term "effective amount" as used herein means a predetermined amount of the compound of this invention sufficient to be effective against HIV in vivo.

Other symbols used herein are:

| | |
|---|---|
| Boc | 1,1-dimethylethoxycarbonyl or tert-butoxycarbonyl |
| Z | benzyloxycarbonyl |
| Ph | phenyl |
| N—Me—Val | N-methylvalyl residue |
| Tbg | 2(S)-amino-3,3-dimethyl-butanoic acid residue |
| Asp(cyPn) | (S)-α-amino-1-carboxycyclopentaneacetic acid residue |
| βMeAsp | 2(S)-amino-3(R)methylbutanedioic acid residue (i.e. the residue of 3(R)-methyl-L-aspartic acid) |
| βMeAsp(OBzl) | O$^4$-benzyl derivative (ester) of βMeAsp |
| βCN-Ala | 2-(S)-amino-3-cyanopropanoic acid residue |

Process

The compounds of formula 1 are composed of four or five structural units or fragments. The two terminal units are an acyl residue (the N-terminus) and either an alkylamino, alkoxy or arylamino residue (the C-terminus). The central units are an amino acid or derived amino acid residue which may be present or absent (see radical A of formula 1), and two non-peptidic fragments (i.e. a 1,3 (S)-diamino-4-phenyl-2(R)-butanol residue and a succinyl residue).

The fragments are linked together by amide bonds, or by an -ester linkage in the instance wherein the C-terminus is an alkoxy residue. This feature in effect allows the compound to be prepared conveniently by methods commonly used in peptide synthesis involving the stepwise coupling of appropriate fragments. Such methods are described in general text books; for example, "Annual Reports In Organic Synthesis—1990", K. Turnbull et al., Eds., Academic Press, Inc., San Diego, Calif., USA, 1990 (and the preceding annual reports), "Vogel's Textbook Of Practical Organic Chemistry", B.S. Furniss et al., Eds, Longman Group Limited, Essex, UK, 1986, and "The Peptides: Analysis, Synthesis, Biology", E. Grass et al., Eds, Academic Press, New York, N.Y., USA, 1979–1987, Volumes 1 to 9.

In general, therefore, the compound of formula 1 can be prepared by a process comprising the sequential stepwise coupling of the appropriate fragments, namely the amino acid or derived amino acid residue which may be present or absent, and the non-peptidic fragments of the compound (including the N-terminal acyl and C-terminal amino or oxy residues), which if required are suitably protected to eliminate competitive reactive sites, and eliminating any protective groups, if present, at the completion of the stepwise coupling to obtain the compound of formula 1.

A common feature of the aforementioned process is the protection of the reactive side chain groups of the various amino acid residues or derived amino acid residues (or, if required, non-peptidic fragments) with suitable protective groups which will prevent a chemical reaction from occurring at that site until the protective group is ultimately removed. Also common is the protection of an α-amino group of a fragment by an α-amino protective group while the free carboxy group of that fragment is coupled with a free α-amino group of a second fragment; the α-amino protective group being one which can be selectively removed to allow a subsequent coupling step to take place at that α-amino group.

The use of coupling agents to promote the dehydrative coupling of a free carboxyl of one reactant with a free amino group of the other reactant is well known; for example, see "The Peptides: Analysis, Synthesis, Biology", Volumes 1 to 8, noted hereinbefore. Examples of suitable coupling agents are 1,1'-carbonyldiimidazole or N,N'-dicyclohexylcarbodiimide. Other examples are 1-hydroxybenzotriazole in the presence of N,N'-dicyclohexylcarbodiimide or N-ethyl-N'-[(3-dimethylamino)propyl]carbodiimide. A very practical and useful coupling agent is the commercially available (benzotriazol-1-yloxy) tris-(dimethylamino)-phosphonium hexafluorophosphate, either by itself or in the presence of 1-hydroxybenzotriazole. Still another very practical and useful coupling agent is the commercially available 2-(1H-benzotriazol-1-yl)-N,-N, N', N'-tetramethyluronium tetrafluoroborate.

The coupling reaction is conducted in an inert solvent, e.g. methylene dichloride, acetonitrile or dimethylformamide. An excess of an organic amine, e.g. diisopropylethylamine or N-methylmorpholine, is added to maintain the reaction mixture at a pH of about eight. The reaction temperature usually ranges from −20° to about 30° C. and reaction time from two to 18 hours.

The process is illustrated by the following reaction scheme wherein A, $R^1$, $R^2$, Q and Y are as defined herein and PG represents an amino protective group (e.g. Boc or Z).

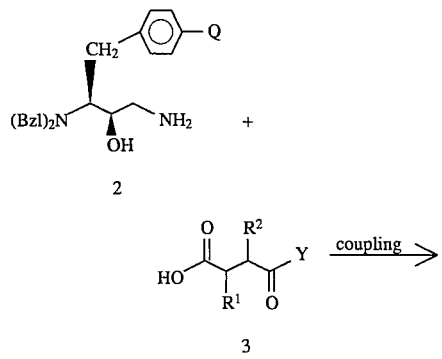

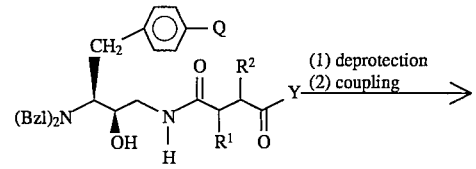

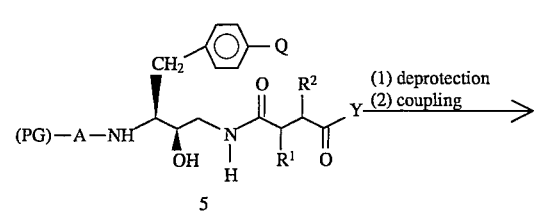

compound of formula 1

The requisite starting material of formula 2 is prepared by lithium aluminum hydride reduction of 3(S)-(dibenzylamino)-2(R)-hydroxy-4-phenylbutanenitrile; the latter compound has been described previously by M. T. Reetz et al., Tetrahedron Lett., 29, 3295 (1988).

The starting materials of formula 3 can be prepared by known methods from known starting materials. For example, the reaction of an appropriately substituted succinic anhydride (corresponding to the succinyl portion of compound 3) with the appropriate amine or alcohol (corresponding to the Y portion of compound 3) at low temperature (−40° to 20° C.) in pyridine solution readily affords the desired succinamoyl derivative or succinic acid monoester of formula 3. Methods for preparing chirally pure substituted succinic anhydrides have been described by T. Polonaki, J. Chem. Soc. Perkin Trans. I, 629 (1988). For still other methods for preparing succinic anhydrides, see *Comprehensive Organic Chemistry*, D. Barton and W. D. Ollis, Eds., Pergamon Press, Oxford, UK, 1979, Vol. 2, pp. 661–694. In turn, the aforementioned appropriate amines or alcohols (including phenols) are commercially available or can be prepared by standard methods; for example, see *Comprehensive Organic Chemistry*, ibid, Vol. 1, pp. 579–662 and Vol. 2, pp. 1–184.

For the acyl portion (i.e. the X radical of formula 1) the appropriate requisite acid starting materials, including those incorporating Het, are well known or can be prepared by known methods; for example, see *Comprehensive Organic Chemistry*, ibid, Vol. 2, pp. 593–622.

The compound of formula 1 of this invention can be obtained in the form of a therapeutically acceptable acid addition salt. Examples of such salts are those with organic acids, e.g. acetic, lactic, succinic, benzoic, salicylic, methanesulfonic or p-toluenesulfonic acid, as well as polymeric acids such as tannic acid or carboxymethyl cellulose, and also salts with inorganic acids such as hydrohalic acids, e.g. hydrochloric acid, or sulfuric acid, or phosphoric acid. If desired, a particular acid addition salt is converted into another acid addition salt, such as a non-toxic, pharmaceutically acceptable salt, by treatment with the appropriate ion exchange resin in the manner described by R. A. Boissonnas et al., Helv. Chim. Acta, 43, 1849 (1960).

In general, the therapeutically acceptable salts of the peptides of formula 1 are biologically fully equivalent to the peptides themselves and are included within the scope of this invention.

BIOLOGICAL ASPECTS

The HIV protease inhibiting properties and the cell protective effect against HIV pathogenesis of the compounds of formula 1, or a therapeutically acceptable salt thereof, can be demonstrated by biochemical, microbiological and biological procedures.

A particular useful procedure for demonstrating the HIV protease inhibiting properties of the compounds of formula 1 or their therapeutically acceptable salts is the "Recombinant HIV Protease HPLC Assay". The procedure is based on the capacity of the test compound to inhibit enzymatic cleavage by HIV protease of a decapeptide (the substrate) having an amino acid sequence which includes a known HIV protease cleavage site of a HIV polyprotein; see H. G. Krausslich et al., Proc. Natl. Acad. Sci. USA, 86, 807 (1989). Details of this assay together with the results obtained for exemplified compounds of formula 1 are described in the examples hereinafter.

The capacity of the compounds of formula 1 or their therapeutically acceptable salts to protect cells against HIV infection can be demonstrated by microbiological procedures for evaluating the inhibitory effect of a test compound on the cytopathogenicity of HIV in human T4 cell lines. Typical of such procedures are those described by S. Harada and N. Yamamoto, Jpn. J. Cancer Res. (Gann), 76, 432 (1985), and S. Harada et al., Science, 229, 563 (1985). An assay based on the latter procedures is described in the examples hereinafter.

When a compound of this invention, or a therapeutically acceptable salt thereof, is used to combat HIV infections in a human, the peptide can be administered orally, topically or parenterally, in a vehicle comprising one or more pharmaceutically acceptable carriers, the proportion of which is determined by the solubility and chemical nature of the compound, the chosen route of administration and standard biological practice. For oral administration, the compound or a therapeutically acceptable salt thereof can be formulated in unit dosage forms such as capsules or tablets each containing a predetermined amount of the active ingredient, ranging from about 5 to 150 mg, in a pharmaceutically acceptable carrier. For topical administration, the compound can be formulated in a pharmaceutically acceptable vehicle containing 0.01 to 2 percent, preferably 0.05 to 1 percent, of the active agent. Such formulations can be in the form of a cream, lotion, sublingual tablet, or preferably a transdermal patch or buccal patch. For parenteral administration, the compound of formula 1 is administered by either intravenous, subcutaneous or intramuscular injection, in compositions with pharmaceutically acceptable vehicles or carriers. For administration by injection, it is preferred to use the compound in solution in a sterile aqueous vehicle which may also contain other solutes such as buffers or preservatives as well as sufficient quantities of pharmaceutically acceptable salts or of glucose to make the solution isotonic.

Suitable vehicles or carriers for the above noted formulations can be found in standard pharmaceutical texts, e.g in "Remington's Pharmaceutical Sciences", 18th ed., Mack Publishing Company, Easton, Penn., 1990.

The dosage of the compound will vary with the form of administration and the particular active agent chosen. Furthermore, it will vary with the particular host under treatment. Generally, treatment is initiated with small dosages substantially less than the optimum dose of the peptide. Thereafter, the dosage is increased by small increments until the optimum effect under the circumstances is reached. In general, the compound is most desirably administered at a concentration level that will generally afford antivirally effective results without causing any harmful or deleterious side effects.

For oral administration, the compound or a therapeutically acceptable salt is administered in the range of 0.5 to 50 mg per kilogram of body weight per day, with a preferred range of 0.5 to 30 mg per kilogram. With reference to systemic administration, the compound of formula 1 is administered at a dosage of 1 µg to 100 µg per kilogram of body weight per day, although the aforementioned variations will occur.

Although the formulations disclosed hereinabove are effective and relatively safe medications for treating HIV infections, the possible concurrent administration of these formulations with other antiviral medications or agents to obtain beneficial results is not excluded. Such other antiviral medications or agents include soluble CD4, zidovudine, didanosine, nevirapine, saquinavir, , 2',3'-dideoxycytidine, trisodium phosphonoformate, ribavarin, acyclovir or antiviral interferons (e.g. α-interferon or interleukin-2).

The following examples illustrate further this invention. Solution percentages or ratios express a volume to volume relationship, unless stated otherwise. Temperatures are given in degrees Celsius. Proton nuclear magnetic resonance (NMR) spectra were recorded on a Bruker 200 MHz or 400 MHz spectrometer (a 400 MHz spectrum being noted as such in the preamble of the spectrum). The chemical shifts of the NMR spectra are reported in parts per million relative to tetramethylsilane as the internal standard. Abbreviations or symbols used herein include Boc: tert-butyloxycarbonyl; tert-Bu: tert-butyl; Bzl: benzyl; DMF: dimethylformamide; HEPES: N-2-hydroxyethylpiperazine-N'-2-ethanesulfonic acid; Et: ethyl; $Et_2O$: diethyl ether; EtOAc: ethyl acetate; HPLC: high performance liquid chromatography; Me: methyl; MeOH: methanol; Ph: phenyl; PhO: phenoxy; Pr: propyl; TBTU: 2-(1 H-benzotriazol-1-yl)-N,N,N',N'-tetramethyluronium tetrafluoroborate; TFA: trifluoroacetic acid; Z: benzyloxycarbonyl.

Example 1

4-[(1-Ethylpropyl)amino]-2(R)-tert-butyl-4-oxobutanoic acid

A solution of 2(R)-tert-butyldihydro-2,5-furandione [10.0 g, 64 mmol; described by T. Polonski, J. Chem. Soc. Perkin Trans. I, 629 (1988)] in pyridine (230 mL) was cooled to −40° C. A solution of 1-ethylpropylamine (6.7 g, 77 mmol) in pyridine (20 mL) was added dropwise over a period of 20 min to the cooled solution. The reaction mixture was allowed to warm to room temperature (10°–22°) and stirred for 3.5 days. Removal of volatiles under reduced pressure gave an oily residue which was dissolved in EtOAc (200 mL) and washed with a 10% aqueous solution of citric acid. The aqueous phase was back-extracted with EtOAc and the combined organic layers where washed with brine and dried over $Na_2SO_4$. The solvent was removed under reduced pressure to give a semi-solid which was coevaporated twice with $Et_2O$ (100 mL) to give a white solid (15.4 g, 99% yield). Mp: 104°–108°. $[\alpha]_D^{24}$ −3.2° (c=1, MeOH). $[\alpha]_{Hg365}^{24}$ −22.2° (c=1, MeOH). $^1H$ NMR ($CDCl_3$, 400 MHz) δ 0.86 (t, J=7.6 Hz, 3H), 0.88 (t, J=7.3 Hz, 3H), 1.02 (s, 9H), 1.35 (m, J=7.0 Hz, 2H), 1.51 (m, J=7.0 Hz, 2H), 2.40 (dd, J=14.5, 3.3 Hz, 1H), 2.53 (dd, J=14.3, 11.4 Hz, 1H), 2.78 (dd, J=11.3, 3.3 Hz, 1H), 3.75 (m , 1H), 5.37 (d, J=8.9 Hz, 1H). FAB-MS (m/z): 243 $(M+H)^+$.

Example 2

1-Amino-3(S)-(dibenzylamino)-4-phenyl-2(R)-butanol

A solution of 3(S)-(dibenzylamino)-2(R)-hydroxy-4-phenylbutanenitrile [50.82 g, 143 mmol] described by M. T.

Reetz et al., Tetrahedron Lett., 29, 3295 (1988)] in anhydrous Et$_2$O (250 mL) was added dropwise over a period of 2 h to a stirred, cooled (0°) mixture of LiAlH$_4$ (8.10 g, 213 mmol) and anhydrous Et$_2$O (500 mL). The mixture was allowed to warm to room temperature while being stirred for 4.5 h. The mixture was cooled again to 0°. EtOAc (100 mL) was added slowly over 15 min. Stirring was continued for 15 min at 0°. A cold (0°) solution of 2N NaOH (250 mL) was added dropwise to the reaction mixture giving a white suspension/emulsion. The cloudy organic supernatant was separated and the remainder of the suspension/emulsion was passed through a 45 μm filter. The filtrate was extracted with EtOAc and the extract was combined with the first organic phase. After drying over NaCl/Na$_2$SO$_4$, the solution was concentrated to a volume of ca 100 mL and allowed to stand at 5° for 18 h. The precipitated material was separated, triturated with hexane (300 mL), collected by filtration, and dried under reduced pressure to give the title compound as a white solid (34 g, 66% yield). Mp: 72°–76°. $[\alpha]_D^{24}$ –1.9° (c=1, MeOH). $[\alpha]_{Hg365}^{24}$ –24.0° (c=1, MeOH). $^1$H NMR (CDCl$_3$, 400 MHz) δ 2.68 (dd, J=12.6, 7.6, 7.2 Hz, 1H), 2.81 (dd, J=12.6, 3.8, 3.5 Hz, 1H), 2.86–3.00 (m, 2H), 3.08 (dd, J=14.1, 7.6, 7.3 Hz, 1H), 3.59 (d, J=13.7 Hz, 2H), 3.69 (m, 1H), 3.71 (d, J=13.7 Hz, 2H), 7.16–7.35 (m, 15H). FAB-MS (m/z): 361 (M+H)$^+$.

Example 3

N$^4$-[3(S)-(Dibenzylamino)-2(R)-hydroxy-4-phenylbutyl]-N$^1$-(1-ethylpropyl)-3(R)-tert-butylbutaneamide A solution of 1-amino-3(S)-(dibenzylamino)-4-phenyl-2(R)-butanol (5.00 g, 13.9 mmol; described in example 2), 4-(1-ethylpropylamino)-2(R)-tert-butyl- 4-oxobutanoic acid (3.70 g, 15.2 mmol; described in example 1), TBTU (5.30 g, 16.5 mmol) and N-methylmorpholine (6 mL, 54.5 mmol) in acetonitrile (60 mL) was stirred 18 h at room temperature. The reaction mixture was concentrated under reduced pressure. The residue was dissolved in EtOAc. The solution was washed with 1N aqueous ammonia (4×) and brine (2×). After drying over a mixture of decolorizing charcoal and Na$_2$SO$_4$, the solvent was removed under reduced pressure. The residue was purified by flash chromatography using 8:2 hexanes/EtOAc (8:2) followed by hexanes/EtOAc (1:1) as eluants. After combining the appropriate fractions and removing the solvent, the resulting yellow residue was triturated with hexanes and dried under reduced pressure to give the title compound as a white solid (4.43 g, 55% yield). Mp: 110°–112°. $[\alpha]_D^{24}$ +6° (c=1, MeOH). $^1$H NMR (CDCl$_3$, 400 MHz) δ 0.82 (s, 9H), 0.86 (t, J=7.3 Hz, 3H), 0.88 (t, J=7.3 Hz, 3H), 1.23–1.38 (m, 2H), 1.43–1.58 (m, 2H), 1.95 (dd, J=11.6, 3.2, 2.9 Hz, 1H), 2.26 (dd, J=13.7, 2.9 Hz, 1H), 2.40 (dd, J=13.4, 11.8 Hz, 1H), 2.93 (m, 1H), 3.02 (m, 1H), 3.18 (dd, J=14.0, 4.1 Hz, 1H), 3.33 (dt, J=14.6, 4.7 Hz, 1H), 3.42 (d, J=13.4 Hz, 2H), 3.58 (broad s, 1H), 3.70 (d, J=13.4 Hz, 2H), 3.70–3.81 (m, 3H), 5.00 (broad t, J=5.5 Hz, 1H), 5.20 (d, J=9.2 Hz, 1H), 7.15 (d, J=7.0 Hz, 3H), 7.20–7.37 (m, 12H). FAB-MS (m/z): 586 (M+H)$^+$.

Example 4

N$^4$-[3(S)-Amino-2(R)-hydroxy-4-phenylbutyl]-N$^1$-(1-ethylpropyl)-3(R)-tert-butylbutanediamide.

The title compound of example 3 (6.43 g, 10.97 mmol) was dissolved in MeOH (100 mL). 20% Pd(OH)$_2$/C (200 mg) and glacial acetic acid (5 mL) were added to the solution. The mixture was stirred under an atmosphere of H$_2$ for 1.5 h. Thereafter, the mixture was filtered through a 45 μM membrane and the filtrate was concentrated under reduced pressure. The residue was dissolved in EtOAc. The solution was washed serially With an aqueous saturated solution of Na$_2$CO$_3$ (3×20 mL) and brine (2×), dried (Na$_2$SO$_4$) and concentrated to give a solid. Trituration of the solid with Et$_2$O afforded the title compound as a white powder (3.53 g, 79% yield) Mp 155°–158°. $[\alpha]_D^{24}$ –14.0° (c=1, MeOH). $^1$H NMR(CDCl$_3$, 400 MHz) δ 0.85 (t, J=7.3 Hz, 3H), 0.87 (t, J=7.3 Hz, 3H), 1.01 (s, 9H), 1.26–1.41 (m, 2H), 1.41–1.58 (m, 2H), 2.36 (dd, J=13.8, 2.9, 2.6 Hz, 1H), 2.43–2.50 (m, 2H), 2.60 (dd, J=13.8, 11.4 Hz, 1H), 2.98–3.09 (m, 2H), 3.15 (m, 1H), 3.52–3.60 (m, 2H), 3.72 (m, 1H), 5.40 (d, J=8.9 Hz, 1H), 6.50 (broad t, J=5.4 Hz, 1H), 7.18–7.33 (m, 5H). FAB-MS (m/z): 406 (M+H)$^+$.

Example 5

N$^1$-(1-Ethylpropyl)-N$^4$-{3(S)-{[N-(2-quinolylcarbonyl)threonyl]amino}-2(R)-hydroxy-4-phenylbutyl}-3(R)-tert-butylbutanediamide a) N$^1$-(1-Ethylpropyl)-N$^4$-(3(S)-{[N-(tert-butyloxycarbonyl)threonyl]amino}-2(R)-hydroxy-4-phenylbutyl}-3(R)-tert-butylbutanediamide: N—Boc—Thr—OH 10 (0.65 g, 2.96 mmol) and the title compound of example 4 (1.09 g, 2.69 mmol) were coupled with TBTU (0.95 g, 2.96 mmol) and N-methylmorpholine (0.90 mL, 8.18 mmol) in DMF (25 mL). After 3 h, the solvent was removed under reduced pressure. The residue was dissolved in EtOAc. The solution was washed with 1N aqueous ammonia and brine, dried (Na$_2$SO$_4$) and concentrated under reduced pressure to give a semisolid. Purification by flash chromatography, using 5% CH$_3$OH in EtOAc as eluant, gave the desired compound as a white solid (1.43 g, 88% yield). The white solid was used in the following step without further purification.

b) N$^1$-(1-Ethylpropyl)-N$^4$-{3(S)-[(threonyl)amino]- 2(R)-hydroxy-4-phenylbutyl}-3(R)-tert-butylbutanediamide:
The product from section (a) of this example (1.43 g, 2.35 mmol) was dissolved in TFA/CH$_2$Cl$_2$ (3:7, 100 mL). The solution was stirred for 20 min at room temperature. The volatiles were removed under reduced pressure to give the desired compound as a solid (1.65 g). The solid was used as such for the following step.

c) The title compound of this example: The crude product from section (b) (1.65 g) and 2-quinolylcarboxylic acid (0.45 g, 2.60 mmol) were coupled using TBTU (0.83 g, 2.58 mmol) and N-methylmorpholine (1.3 mL, 11.8 mmol) in DMF (25 mL). After 4 h at room temperature, the solvent was removed under reduced pressure. The residue was dissolved in EtOAc and the solution was washed with 1N aqueous ammonia and brine. After drying over Na$_2$SO$_4$, the solvent was evaporated under reduced pressure. The residue was purified by flash chromatography using EtOAc/hexane/MeOH (70:25:5). The resulting material was purified further by reversed-phase HPLC (using 0.06% TFA in CH$_3$CN/0.06% TFA in water as the mobile phase) to give the title compound of this example as a white solid (0.97 g, 62% yield, after lyophilization). Mp 110°–125°. $[\alpha]_D^{24}$ +21.4° (c=1, MeOH). $^1$H NMR(CDCl$_3$, 400 MHz) δ 0.83 (t, J=7.6 Hz, 3H), 0.86 (t, J=7.6 Hz, 3H), 1.05 (s, 9H), 1.20 (d, J=6.4 Hz, 3H), 1.24–1.38 (m, 2H), 1.4–1.57 (m, 2H), 2.43 (d, J=11.5 Hz, 1H), 2.55–2.73 (m, 3H), 3.11 (dd, J=13.3, 4.5 Hz, 1H), 3.20 (m, 1H), 3.63 (m, 1H), 3.70 (m, 2H), 4.27 (m, 1H), 4.4–4.7 (m, 4H), 5.65 (d, J=8.9 Hz, 1H), 6.83 (q, J=7.3 Hz, 1H), 6.87–6.98 (m, 3H), 7.01 (t, J=5.9 Hz, 1H), 7.08 (d, J=7.0 Hz, 2H), 7.66 (dt, J=7.0, 1.0 Hz, 1H), 7.82 (dt, J=8.3, 1.3 Hz, 1H), 7.92 (d, J=8.0 Hz, 1H), 8.19 (d, J=8.6 Hz, 1H), 8.25 (d, J=8.6 Hz, 1H), 8.36 (d, J=8.6 Hz, 1H), 8.85 (d, J=8.3 Hz, 1H). FAB -MS (m/z): 662 (M+H)$^+$, 684 (M+Na)$^+$.

Example 6

Preparation of N$^1$-(1-Ethylpropyl)-N$^4$-{3(S)-{{(2,6-dimethylphenoxy)acetyl}amino}-2(R)-hydroxy-4-phenylbutyl}-3(R)-tert-butylbutanediamide The title compound of example 4 (0.020 g, 0.049 mmol), (2,6-dimethylphenoxy)acetic acid (0.01 g, 0.053 mmol) and TBTU (0.020 g, 0.06 mmol) were dissolved in DMF (1.5 mL). N-Methylmorpholine (100 µL, 0.9 mmol) was added to the solution. The reaction mixture was stirred at room temperature for 2.5 h and then quenched by the addition of 1N aqueous NH$_4$OH. The mixture was subjected directly to HPLC on a C-18 reversed-phase column using 0.06% aqueous TFA—0.06% TFA in acetonitrile gradients. By combining the appropriate fractions, the title compound was obtained as an amorphous solid after lyophilization (0.012 g). $^1$H NMR (CDCl$_3$, 400 MHz) δ 0.86 (t, J=7.3 Hz, 3H), 0.88 (t, J=7.3 Hz, 3H), 1.09 (s, 9H), 1.25–1.4 (m, 2H), 1.44–1.58 (m, 2H), 2.12 (s, 6H), 2.41 (d, J=10.8 Hz, 1H), 2.59 (m, 1H), 2.89 (dd, J=14.3, 8.9 Hz, 1H), 3.04 (dt, J=14.0, 4.8 Hz, 1H), 3.27 (dd, J=14.3, 3.8 Hz, 1H), 3.66 (m, 1H), 3.73 (m, 1H), 3.87 (ddd, J=17.2, 7.0, 2.6 Hz, 1H), 4.08 (d, J=15.0 Hz, 1H), 4.22 (d, J=15.0 Hz, 1H), 4.32 (dq, J=8.4, 5.1 Hz, 1H), 5.45 (d, J=9.5 Hz, 1H), 6.88 (d, J=8.6 Hz, 1H), 6.93–7.02 (m, 3H), 7.2–7.32 (m, 5H). FAB-MS (m/z): 568 (M+H)$^+$, 590 (M+Na)$^+$.

The (2,6-dimethylphenoxy)acetic acid, used in this example, was prepared as follows: 2,6 -Dimethylphenol (500 g, 4.09 mol), ethyl bromoacetate (480 mL, 4.30 mol) and anhydrous K$_2$CO$_3$ (690 g, 5.0 mol) were suspended in acetone (2 L) and the mixture was stirred for 56 h at room temperature, and then heated at reflux for 24 h. 1N NaOH (1 L) was added and the heating was continued for another 4 h. Thereafter, solid NaOH (150 g, 3.75 mol) was added and the heating was continued for an additional 48 h. After cooling to room temperature, the acetone was removed under reduced pressure. The residue was adjusted to pH 1 with concentrated HCl. The resulting tan colored precipitate was collected, washed with water, air dried and crystallized from isopropanol to give 480 g of material. The latter material was purified by recrystallization from EtOAc to give (2,6 -dimethylphenoxy)acetic acid as white needles (386 g, 52% yield). Mp 137.5°–139°. $^1$H NMR (CDCl$_3$) δ 2.30 (s, 6H), 4.50 (s, 2H), 7.0 (m, 3H), 10.35 (broad s, 1H). MS(Cl/isooctane) m/z: 181 (M+1). A second crop of product (73.7 g) of comparable purity was obtained by concentration of the mother liquors. The total yield of product was 459.7g (62% yield).

By following the latter procedure and replacing 2,6-dimethylphenol with the appropriate phenol as starting material, other phenoxyacetic acid derivatives can be obtained. For example, replacement with 2,4-dimethylphenol afforded (2,4 -dimethylphenoxy)acetic acid.

By following the procedures of examples 1 to 6 and using the appropriate intermediates, other examples of the compound of formula 1, such as those exemplified in the tables of the following example, can be prepared.

Example 7

The following Tables 1 to 8 list the results obtained for exemplified compounds of formula 1 when tested in the recombinant HIV protease HPLC assay described by P. C. Anderson, S. Rakhit and C. Yoakim in the European patent application 443 560, published Aug. 28, 1991. The results from this assay are reported as IC$_{50}$'s and represent the concentration of the test compound which causes a 50% inhibition of HIV protease.

In addition, Tables 1 to 8 list the results for exemplified compounds of formula 1 when assayed for antiviral (anti-HIV) effects according to the following protocol which is based on a cell culture assay previously described by Harada et al., supra. Transformed cells are used because of the rapidity with which HIV will replicate in the cells.

Cell Culture Assay

1. The test compound is dissolved in dimethylsulfoxide to a concentration of 5 mg/mL. The resultant solution .can be stored at 4° until use.
2. The resultant solution is diluted in RPMI 1640 (Gibco Laboratories, St. Lawrence, Mass., USA) to four times (4×) the final concentration which is to be tested. Once diluted in RPMI 1640, the solution is used in the cell culture assay within 4 h.
3. The latter solution (50 µL) is added to triplicate wells of a 96 well flat bottomed microtiter plate. RPMI (50 µL) also is added to control wells.
4. C8166 cells (5×10$^4$) in 50 µL of HEPES-buffered RPMI 1640 (pH=7.2), 10% heat inactivated fetal calf serum (FCS), 12.5 µL/mL gentamicin (complete media) are added to all wells.
5. Fifty times TCID$_{50}$ of H9/HTLV-IIIB stock (stored in liquid nitrogen as cell culture supernatant in 50% FCS) in 100 µL of complete media is added to all wells. The infectious titer of the virus stocks is as previously determined by end point dilution on C8166 cells. The titer of stocks are stable for 6–12 months when stored at −193°.
6. Microtiter plates are then placed on level shelves of a 37°, 5% CO$_2$ humidified incubator for 72 h.
7. Plates are then removed and centers of syncytia are counted in each well by low power phase contrast light microscopy. Each cluster of cells which shows evidence of any syncytia formation is counted as one center of syncytia. Control wells should have between 25 and 75 centers of syncytia per well.
8. Percent inhibition of syncytia formation is calculated by the formula:

$$\% \text{ inhibition} = 100 \times \frac{\left(\begin{array}{c}\text{\# syncytial centers} \\ \text{in control wells}\end{array}\right) - \left(\begin{array}{c}\text{\# syncytial centers in} \\ \text{test wells}\end{array}\right)}{\left(\begin{array}{c}\text{\# syncytial centers} \\ \text{in control wells}\end{array}\right)}$$

The concentration of the test compound which causes a 50% inhibition of syncytia formation, i.e. the EC$_{50}$, is determined by using the technique of serial dilution of the working solution at step 3 and graphically plotting the observed percent inhibition of syncytia formation against the various concentrations of the test compound.

In the following tables, assay results are listed for the exemplified compounds from the aforementioned recombinant HIV protease HPLC assay under the heading IC$_{50}$ (nM) and from the cell culture assay under the heading EC$_{50}$ (nM). Note that for some of the compounds listed in tables, the EC$_{50}$'s have not been determined (ND).

TABLE 1

Compound of formula 1 having the structure

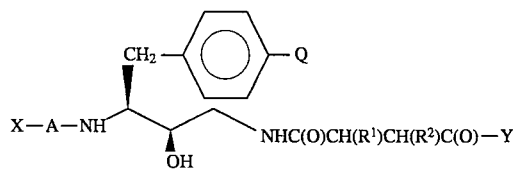

wherein the carbon atom bearing $R^1$ has the (R) configuration, $R^1$ is 1,1-dimethylethyl, $R^2$ and Q are each H, Y is $NHCHEt_2$ and X and A are designated as follows:

| Entry No | X | A | FAB/MS (m/z) $(M + H)^+$ | $IC_{50}$ (nM) | $EC_{50}$ (nM) |
|---|---|---|---|---|---|
| 1 | Boc | Tbg | 619 | 100 | ND |
| 2 | Boc | Asp | 621 | 90 | ND |
| 3 | 1-oxo-3-piperidinopropyl | Asn | 659 | 88 | ND |
| 4 | Boc | βMeAsp—(Bzl) | 725 | 80 | ND |
| 5 | 1,2,3,4-tetrahydroiso-quinol-3 (R or S)-ylcarbonyl | Asn | 679 | 32 | ND |
| 6 | 2-quinolylcarbonyl | Ser | 648 | 27 | 420 |
| 7 | 1-isoquinolylcarbonyl | Asn | 675 | 20 | ND |
| 8 | Z | Gln | 668 | 19 | ND |
| 9 | $PhCH_2CH_2C(O)$ | Asn | 652 | 15 | 1900 |
| 10 | 8-quinolylcarbonyl | Asn | 675 | 15 | 270 |
| 11 | (1-methyl-2-indolyl)carbonyl | Asn | 677 | 14 | 660 |
| 12 | $PhCH_2CH_2CH_2CH_2C(O)$ | Asn | 702* | 13 | ND |
| 13 | Z | N—MeVal | 653 | 12 | 1900 |
| 14 | $PhCH_2NHC(O)$ | Asn | 653 | 11 | ND |
| 15 | 4-quinolylcarbonyl | Asn | 675 | 9 | 450 |
| 16 | Boc | βMeAsp | 635 | 7 | ND |
| 17 | PhCH=CHC(O) | Asn | 650 | 7 | 1400 |
| 18 | 3-isoquinolylcarbonyl | Asn | 675 | 5 | 220 |
| 19 | $PhNHCH_2C(O)$ | Asn | 653 | 5 | ND |

| | Compound of formula 1 | | FAB/MS (m/z) | $IC_{50}$ | $EC_{50}$ |
|---|---|---|---|---|---|
| No | X | A | $(M + H)^+$ | (nM) | (nM) |
| 20 | Z | Asn | 654 | 5 | 480 |
| 21 | $PhCH_2CH_2C(O)$ | Asn | 666 | 5 | 1100 |
| 22 | 2-quinolylcarbonyl | βMeAsp | 690 | 5 | ND |
| 23 | 2-quinolylcarbonyl | Thr | 662 | 4 | 52** |
| 24 | 1,2,3,4-tetrahydroisoquin-ol-3(R or S)-ylcarbonyl | Asn | 679 | 4 | ND |
| 25 | (4-methoxy-2-quinolyl)carbonyl | Asn | 705 | 4 | 164 |
| 26 | 2-quinoxalinylcarbonyl | Thr | 663 | 4 | 65 |
| 27 | 2-quinolylcarbonyl | Tbg | 674 | 4 | 83 |
| 28 | $CH_3C(O)$ | Val | 547 | 4 | 530 |
| 29 | 2-quinolylcarbonyl | Val | 660 | 3 | 52 |
| 30 | 2,3-dihydroindol-2(R or S)-ylcarbonyl | Asn | 665 | 3 | ND |
| 31 | 2-quinoxalinylcarbonyl | Val | 661 | 3 | 25 |
| 32 | Z | Val | 639 | 3 | 63 |
| 33 | 2-quinolylcarbonyl | Asp—(cyPn) | 730 | 3 | ND |
| 34 | Z | Tbg | 653 | 3 | 65 |
| 35 | 2-quinolylcarbonyl | Asn | 675 | 3 | 130 |
| 36 | 2-quinoxalinylcarbonyl | Asn | 676 | 3 | 260 |
| 37 | 2-quinolylcarbonyl | βCN—Ala | 657 | 3 | 34 |
| 38 | 6-quinolylcarbonyl | Asn | 675 | 2 | ND |
| 39 | 3-quinolylcarbonyl | Asn | 675 | 2 | ND |
| 40 | $PhCH_2CH_2OC(O)$ | Asn | 668 | 4 | 570 |
| 41 | $PhOCH_2C(O)$ | Thr | 641 | 3 | 170 |

*$(M + Na)^+$
**the title compound of example 5

TABLE 2

Compound of formula 1 wherein the carbon atom bearing $R^1$ has the (R) configuration, X is 2-quinolylcarbonyl, $R^1$ is 1,1-dimethylethyl, $R^2$ and Q are each H, and A and Y are designated as follows:

| Entry No | A | Y | FAB/MS (m/z) $(M + H)^+$ | $IC_{50}$ (nM) | $EC_{50}$ (nM) |
|---|---|---|---|---|---|
| 42 | Thr | (2,6-diisopropylphenyl)-amino | 752 | 19 | 830 |
| 43 | Thr | (2,6-diethylphenyl)amino | 724 | 5 | 30 |
| 44 | Asn | $NHCHPr_2$ | 703 | 4 | 57 |
| 45 | Asn | 1-isopropyl-2-methylpropylamino | 703 | 4 | 150 |
| 46 | Thr | (2,6-dimethylphenyl)-amino | 696 | 2 | 30 |

TABLE 3

Compound of formula 1 wherein $R^2$ and Q are each hydrogen and X, A, $R^1$ and Y are designated as follows, the compound being a mixture of (R) and (S) diastereoisomers with respect to the asymmetric carbon atom bearing $R^1$.

| Entry No | X | A | $R^1$ | Y | FAB/MS (m/z) $(M + H)^+$ | $IC_{50}$ (nM) | $EC_{50}$ (nM) |
|---|---|---|---|---|---|---|---|
| 47 | Z | Asn | $(CH_3)_3C$ | $OCHEt_2$ | 655 | 51 | ND |
| 48 | Z | Asn | $(CH_3)_2CH$ | $NHCHEt_2$ | 640 | 32 | ND |
| 49 | Z | Asn | $(CH_3)_3C$ | $NHCHEt_2$ | 654 | 13 | 1300 |
| 50 | 2-quinolylcarbonyl | Asn | $(CH_3)_2CH$ | $NHCHEt_2$ | 661 | 9 | ND |
| 51 | Z | Val | $(CH_3)_3C$ | $NHCMe_3$ | 625 | 7 | 200 |
| 52 | 2-quinolylcarbonyl | Asn | $(CH_3)_3C$ | $NHCHEt_2$ | 675 | 6 | 130 |
| 53 | Z | Tbg | $(CH_3)_3C$ | $NHCHEt_2$ | 653 | 6 | 90 |

TABLE 4

Compound of formula 1 wherein $R^1$ and Q are each hydrogen and X, A, $R^2$ and Y are designated as follows, the compound being a mixture of (R) and (S) diastereoisomers with respect to the asymmetric carbon atom bearing $R^2$.

| Entry No | X | A | $R^2$ | Y | FAB/MS (m/z) $(M + H)^+$ | $IC_{50}$ (nM) | $EC_{50}$ (nM) |
|---|---|---|---|---|---|---|---|
| 54 | Z | Val | $(CH_3)_3CCH_2$ | $NHCHEt_2$ | 653 | 50 | ND |

TABLE 5

Compound of formula 1 wherein Q is H and X, A, $R^1$, $R^2$ and Y are designated as follows, the compound being a mixture of cis (R,S) isomers with respect to the carbon atoms bearing $R^1$ and $R^2$.

| Entry No | X | A | $R^1 R^2$ | Y | FAB/MS (m/z) $(M + H)^+$ | $IC_{50}$ (nM) | $EC_{50}$ (nM) |
|---|---|---|---|---|---|---|---|
| 55 | Z | Val | $—(CH_2)_4—$* | $NHCH_2—CMe_3$ | 637 | 66 | ND |
| 56 | Z | Val | $—(CH_2)_4—$* | $NHCHPr_2$ | 665 | 29 | ND |
| 57 | Z | Val | $—(CH_2)_4—$* | $NHCHEt_2$ | 637 | 14 | ND |

*Indicating that $R^1$ and $R^2$ together with the carbon atoms to which they are attached form a 1,2-cyclohexanediyl

TABLE 6

| Entry No | Compound of formula 1 | FAB/MS (m/z) $(M + H)^+$ | $IC_{50}$ (nM) | $EC_{50}$ (nM) |
|---|---|---|---|---|
| 58 | 3(R)-tert-butyl-4-{2(R)-hydroxy-4-phenyl-3(S)-{[N-(2-quinolylcarbonyl)threonyl]-amino}butylamino}-4-oxobutyric acid isopropyl ester | 635 | 46 | ND |
| 59 | 3(R)-tert-butyl-4-{2(R)-hydroxy-4-phenyl-3(S)-{[N-(2-quinolylcarbonyl)asparaginyl]-amino}butylamino}-4-oxobutyric acid 1-ethylpropyl ester | 676 | 7 | 570 |
| 60 | $N^4$-{3(S)-{[N-benzyloxycarbonyl)-tert-butylglycyl]amino}-2(R)-hydroxy-4-phenylbutyl}-$N^1$-(1-ethylpropyl)-3(S)-tert-butylbutanediamide | 653 | 29 | ND |

TABLE 6-continued

| Entry No | Compound of formula 1 | FAB/MS (m/z) (M + H)+ | IC50 (nM) | EC50 (nM) |
|---|---|---|---|---|
| 61 | N4-{3(S)-{[N-benzyloxycarbonyl)valyl]amino}-2(R)-hydroxy-4-phenylbutyl}-N1-(1-ethylpropyl)-2(R)-tert-butylbutanediamide | 639 | 13 | ND |
| 62 | N1-(1-ethylpropyl)-N4-{3(S)-{[N-(2-quinolylcarbonyl)-threonyl]amino}-2(R)-hydroxy-4-(4-hydroxyphenyl)butyl}-3(R)-tert-butylbutanediamide | 678 | 61 | ND |
| 63 | N1-(1-ethylpropyl)-N4-{3(S)-{{(2,6-dimethylphenoxy)-acetyl}amino}-2(R)-hydroxy-4-(4-hydroxyphenyl)butyl}-3(R)-tert-butylbutanediamide | 584 | 3.1 | 110 |

TABLE 7

Compound of Formula 1 having the structure

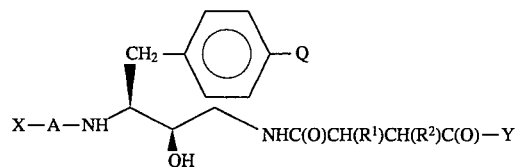

wherein A is absent, the carbon atom bearing $R^1$ has the (R) configuration, $R^1$ is tert-Bu, $R^2$ and Q are each H, Y is $NHCHEt_2$ and X is designated as follows:

| Entry No | X | FAB/MS (m/z) (M + H)+ | IC50 (nM) | EC50 (nM) |
|---|---|---|---|---|
| 64 | (1-methyl-2-indolyl)carbonyl | 563 | 8.9 | 640 |
| 65 | (4-chlorophenyl)carbonyl | 544 | 8.7 | 845 |
| 66 | (2,4-dichlorophenyl)carbonyl) | 578 | 4.7 | 680 |
| 67 | (2,3,6-trichlorophenyl)carbonyl | 614 | 6.0 | 360 |
| 68 | (2-methylphenyl)carbonyl | 524 | 6.4 | 375 |
| 69 | (3-amino-2-methylphenyl)carbonyl | 539 | 5.3 | 258 |
| 70 | (2,4,6-trimethylphenoxy)acetyl | 582 | 4.6 | 1200 |
| 71 | (2,6-dimethylphenoxy)acetyl* | 568 | 3.5 | 645 |

*the title compound of example 6

TABLE 8

Compound of formula 1 having the structure

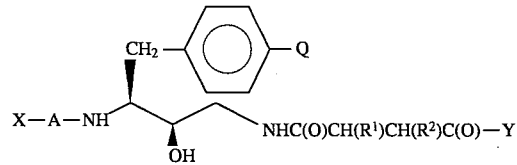

wherein A is absent, the carbon atom bearing $R^1$ has the (R) configuration, $R^1$ is tert-Bu, $R^2$ and Q are each H, Y is (2,6-dimethylphenyl)amino and X is designated as follows:

| Entry No | X | FAB/MS (m/z) (M + H)+ | IC50 (nM) | EC50 (nM) |
|---|---|---|---|---|
| 72 | Z | 574 | 3.0 | 360 |
| 73 | (2,6-dimethylphenoxy)acetyl | 602 | 2.6 | 620 |
| 74 | (2,5-dimethylphenyl)carbonyl | 572 | 2.0 | 370 |

Still other compounds are:

N¹-(1-ethylpropyl)-N⁴-{3(S)-{{(2,5-dimethylphenyl)carbonyl}amino}-2(R)-hydroxy-4-(4-hydroxyphenyl)butyl}-3(R)-tert-butylbutanediamide, N¹-(2,6-dimethylphenyl)-N⁴-{3(S)-{{2,5-dimethylphenyl)carbonyl}amino}-2(R)-hydroxy-4-(4-hydroxyphenyl)butyl }-3(R)-tert-butylbutanediamide, N¹-(1-ethylpropyl)-N⁴-{3(S)-{{2,6-dimethylphenyl)carbonyl}amino}-2(R)-hydroxy-4-(4-hydroxyphenyl)butyl}-3(R)-tert-butylbutanediamide, N¹-(2,6-dimethylphenyl)-N⁴-{3(S)-{{2,6-dimethylphenyl)carbonyl}amino}-2(R)-hydroxy-4-(4-hydroxyphenyl)butyl}-3(R)-tert-butylbutanediamide, N¹-(1-ethylpropyl)-N⁴-(3(S)-{{2,6-dimethyl)acetyl}amino}-2(R)-hydroxy-4-(4-hydroxyphenyl)butyl}-3(R)-tert-butylbutanediamide, and N¹-(2,6-dimethylphenyl)-N⁴-{3(S)-{{2,6-dimethylphenoxy)acetyl}amino)-2(R)-hydroxy-4-(4-hydroxyphenyl)butyl}-3(R)-tert-butylbutanediamide.

We claim:

1. A compound of formula 1

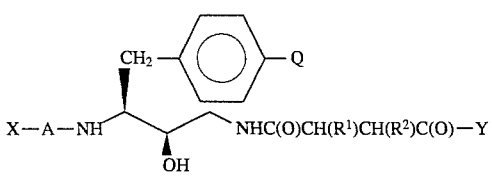

wherein X is R³OC(O), R³C(O) or R³NHC(O) wherein R³ is (i) lower alkyl, (ii) lower cycloalkyl, (iii) phenyl; phenyl monosubstituted with halo, hydroxy, amino, lower alkyl or lower alkoxy; or phenyl disubstituted or trisubstituted with the same or different substituent selected from the group consisting of halo, amino and lower alkyl;

(iv) phenyl(lower)alkyl or phenyl(lower)alkyl wherein the aromatic portion thereof is monosubstituted with halo, hydroxy, lower alkyl or lower alkoxy, (v) phenyl(lower)alkenyl, (vi) 1-naphthyl or 2-naphthyl, (vii) Het or Het-(lower alkyl) wherein Het represents, a five- or six-membered monocyclic, or a nine- or ten-membered bicyclic, radical containing one or two heteroatoms selected from nitrogen, oxygen and sulfur, the heterocyclic radical being either unsubstituted or having one or two of the same or different substituents selected from the group consisting of halo, hydroxy, amino, lower alkyl or lower alkoxy; or X is R³ᴬNHCH₂C(O) wherein R³ᴬ is lower alkyl or phenyl, or X is R³ᴮOCH₂C(O) wherein R³ᴮ is phenyl, phenyl monosubstituted with halo or lower alkyl, or phenyl disubstituted or trisubstituted with the same or different substituent selected from the group of halo and lower alkyl;

A is absent or A is a divalent radical NR⁴CHR⁵C(O) wherein R⁴ is hydrogen or lower alkyl, R⁵ is lower alkyl, 1-carboxycyclobut-1-yl, 1-carboxycyclopent-1-yl, or lower alkyl monosubtituted with carboxy, carbamyl, (lower alkoxy)carbonyl, benzyloxycarbonyl, hydroxy, cyano or benzyloxy, and the carbon atom bearing R⁵ has the (S) configuration.

R¹ is lower alkyl and R² is hydrogen, or R¹ is hydrogen and R² is lower alkyl, or R¹ and R² together with the carbon atoms to which they are attached form a 1,2-cyclohexanediyl;

Q is hydrogen, hydroxy, halo or lower alkoxy; and

Y is (1–8C)alkylamino, (1–8C)alkoxy, phenylamino or phenylamino having one or two of the same or different substituents on the phenyl portion thereof selected from the group consisting of lower alkyl, lower alkoxy, hydroxy, halo, amino or lower alkylamino; or a therapeutically acceptable acid addition salt thereof.

2. A compound as claimed in claim 1 wherein X is (i) R³OC(O) wherein R³ is lower alkyl, lower cycloalkyl, phenyl, phenyl(lower alkyl) or phenyl(lower)alkyl wherein position 4 of the phenyl portion is substituted with halo, lower alkyl or lower alkoxy;

(ii) R³C(O) wherein R³ is lower alkyl; lower cycloalkyl; phenyl; phenyl monosubstituted with halo, hydroxy, lower alkyl or lower alkoxy; phenyl disubstituted or trisubstituted with the same or different substituent selected from the group consisting of chloro, fluoro, amino or methyl; phenyl(lower)alkyl; phenyl(lower)-alkyl monosubstituted at position 4 of the phenyl portion with halo, hydroxy, lower alkyl or lower alkoxy; phenyl(lower)alkenyl; 1-naphthyl; 2-naphthyl; Het, Het-CH₂ or Het-CH₂CH₂ wherein Het is as defined hereinabove; or (phenylamino)methyl; or (iii) R³NHC(O) wherein R³ is lower alkyl; lower cycloalkyl; phenyl; phenyl monosubstituted with halo, lower alkyl or lower alkoxy; benzyl or benzyl monosubstituted at position 4 of the phenyl portion with halo, lower alkyl or lower alkoxy; or X is R³ᴬNHCH₂C(O) wherein R³ᴬ is lower alkyl or phenyl, or X is R³ᴮOCH₂C(O) wherein R³ᴮ is phenyl or phenyl mono-, di- or trisubstituted with lower alkyl or halo at a position or positions selected from the group consisting of positions 2, 4 and 6;

A is absent or the divalent radical NR⁴CHR⁵C(O) wherein R⁴ is hydrogen or methyl and R⁵ is as defined hereinabove;

R¹ is 1-methylethyl, 1,1-dimethylethyl, 1,1 -dimethylpropyl, 2,2,-dimethylpropyl, 3-methylbutyl, 3,3-dimethylbutyl, 4-methylpentyl, 4,4 -dimethylpentyl and R² is hydrogen, or R¹ is hydrogen and R² is 1-methylethyl, 1,1-dimethylethyl, 1,1 -dimethylpropyl, 2,2-dimethylpropyl, 3-methylbutyl, 3,3-dimethylbutyl, 4-methylpentyl or 4,4-dimethylpentyl, or R¹ and R² together with the carbon atoms to which they are attached form a 1,2-cyclohexanediyl; and Q and Y are as defined in claim 1; or a therapeutically acceptable acid addition salt thereof.

3. A compound as claimed in claim 2 wherein X is (i) R³OC(O) wherein R³ is isopropyl, tert-butyl, benzyl or 2-phenylethyl;

(ii) R³C(O) wherein R³ is methyl, ethyl, propyl, cyclopropyl, cyclohexyl, phenyl, 4-chlorophenyl, 2-fluorophenyl, 2,4-dichlorophenyl, 2,6-dichlorophenyl, 2,3,6-trichlorophenyl, 2-methylphenyl, 4-methylphenyl, 2,4-dimethylphenyl, 2,5-dimethylphenyl, 2,6-dimethylphenyl, 3-amino-2-methylphenyl, benzyl, (4-fluorophenyl)methyl, (4-methoxyphenyl)methyl, 2-phenylethyl, 3-phenylpropyl, 4-phenylbutyl, 5-phenylpentyl, 2-(4-fluorophenyl)ethyl, 2-(4-hydroxyphenyl)butyl, (4-methoxyphenyl)butyl, 3-(4-methoxyphenyl)propyl, 1 oxo-3-phenyl-2-propenyl, 1-naphthyl, 2-naphthyl, 2 -furyl, 2-thienyl, 2-pyridinyl, 4-pyridinyl, 4 -thiazolyl, 4-isoxazolyl, 2-quinolyl, 3-quinolyl, 4 -quinolyl, 6-quinolyl, 8-quinolyl, 4-methoxy-2-quinolyl, 1-isoquinolyl, 3-isoquinolyl, 2 -quinoxalinyl, 1-methyl-2-indolyl, 2,3-dihydroindol- 2(R or S)-yl, 1,2,3,4-tetrahydroisoquinol-3(R or S)-yl, 2-pyridinylmethyl, 2-morpholinoethyl, 2 -piperidinoethyl, 3-(4-thiazolyl)propyl, or (phenylamino)methyl;

(iii) R³NHC(O) wherein R³ is lower alkyl, benzyl or benzyl monosubstituted on the aromatic portion thereof with fluoro, methyl or methoxy;

23

X is R³ᴬNHCH₂C(O) wherein R³ᴬ is methyl or phenyl, or X is R³ᴮOCH₂C(O) wherein R³ᴮ is phenyl, 2-methylphenyl, 2,4-dimethylphenyl, 2,6-dimethylphenyl, 2,4,6-trimethylphenyl, 4-chlorophenyl or 4-fluorophenyl;

A is absent or NR⁴CHR⁵C(O) wherein R⁴ is hydrogen or methyl and R⁵ is 1-methylethyl, 1,1-dimethylethyl, 1-methylpropyl, 2-methylpropyl, 1-carboxycyclopent-1-yl, CH₂C(O)OH, (R)—CH(CH₃)C(O)OH, CH₂CH₂C(O)OH, CH₂C(O)NH₂, CH₂CH₂C(O)NH₂, CH₂C(O)OMe, (R)—CH(CH₃)C(O)OBzl, CH₂OH, CH(OH)CH₃ or CH₂CN;

R¹ is 1,1-dimethylethyl, 2,2-dimethylpropyl, 1-methylbutyl, 3,3-dimethylbutyl or 4,4-dimethylpentyl and R² is hydrogen, or R¹ is hydrogen and R² is tert-butyl, 2,2-dimethylpropyl, 1-methylbutyl, 3,3-dimethylbutyl or 4,4-dimethylpentyl; Q is hydrogen, hydroxy or methoxy; and Y is isopropylamino, tert-butylamino, 1-methylpropylamino, 2-methylpropylamino, 1-ethylpropylamino, 1-isopropyl-2-methylpropylamino, 1-ethylbutylamino, 1-propylbutylamino, isopropoxy, 1-ethylpropoxy, phenylamino or phenylamino having one or two of the same or different substituents selected from the group consisting of methyl, ethyl, propyl, isopropyl, hydroxy, fluoro or chloro; or a therapeutically acceptable acid addition salt thereof.

4. A compound as claimed in claim 3 wherein X is tert-butoxycarbonyl, benzyloxycarbonyl, (2-phenylethoxy)carbonyl, acetyl, benzoyl, (2,4-dichlorophenyl)carbonyl, (2,3,6-trichlorophenyl)carbonyl, (2-methylphenyl)carbonyl, (2,5-dimethylphenyl)carbonyl, (2,6-dimethylphenyl)carbonyl, (3-amino-2-methylphenyl)carbonyl, phenoxymethylcarbonyl, 2-quinolylcarbonyl, 3-quinolylcarbonyl, 4-quinolylcarbonyl, 6-quinolylcarbonyl, 8-quinolylcarbonyl, 4-methoxy-2-quinolylcarbonyl, 1-isoquinolylcarbonyl, 3-isoquinolylcarbonyl, 2-quinoxalinylcarbonyl, 1-methyl-2-indolylcarbonyl, 2,3-dihydroindol-2(R or S)-ylcarbonyl, 1,2,3,4-tetrahydroisoquinol-3(R or S)-ylcarbonyl, 1-oxo-3-piperidinopropyl, (phenylamino)methylcarbonyl or (benzylamino)carbonyl; A is Val, N—MeVal, Tbg, Ile, Leu, Asp-(cyPn), Asp, βMeAsp, Glu, Asn, Gln, βMeASp(OBzl), Ser, Thr or βCN-Ala; R¹ is 1,1-dimethylethyl; R² is hydrogen; Q is hydrogen or hydroxy; Y is 1-ethylpropylamino, 1-isopropyl-2-methylpropylamino, 1-propylbutylamino, isopropoxy, 1-ethylpropoxy, phenylamino, (2,6-dimethylphenyl)amino, (2,6-diethylphenyl)amino or (2,6-diisopropylphenyl)amino; and the asymmetric carbon atom bearing R¹ has the (R) configuration.

5. A compound as claimed in claim 3 wherein X is (2-methylphenoxy)acetyl, (2,4-dimethylphenoxy)acetyl, (2,6-dimethylphenoxy)acetyl or (2,4,6-trimethylphenoxy)acetyl, A is absent, R¹ is 1,1-dimethylethyl, R² is hydrogen, Q is hydrogen or hydroxy, and Y is as defined in the last instance; and the asymmetric carbon atom bearing R¹ has the (R) configuration.

6. A compound as claimed in claim 1 wherein A is benzyloxycarbonyl, 2-quinolylcarbonyl or 2-quinoxyalinylcarbonyl, A is Val, Tbg, Asn or Thr, R¹ is 1,1-dimethylethyl, R² is hydrogen, Q is hydrogen or hydroxy, Y is 1-ethylpropylamino or (2,6-dimethylphenyl)amino, and the asymmetric carbon atom bearing R¹ has the (R) configuration.

7. A compound of claim 1 selected from the group consisting of:

24

(i) a compound of formula 1 wherein the carbon atom bearing R¹ has the (R) configuration, R¹ is 1,1-dimethylethyl, R² and Q are each H, Y is NHCHEt₂ and X and A are defined by one of the following combinations thereof:

| COMBINATION (X and A) | |
| --- | --- |
| X | A |
| Boc | Tbg |
| Boc | Asp |
| 1-oxo-3-piperidinopropyl | Asn |
| Boc | βMeAsp-(Bzl) |
| 1,2,3,4-tetrahydroisoquinol-3(R or S)-ylcarbonyl | Asn |
| 2-quinolylcarbonyl | Ser |
| 1-isoquinolylcarbonyl | Asn |
| Z | Gln |
| PhCH₂CH₂C(O) | Asn |
| 8-quinolylcarbonyl | Asn |
| (1-methyl-2-indolyl)carbonyl | Asn |
| PhCH₂CH₂CH₂C(O) | Asn |
| Z | N—MeVal |
| PhCH₂NHC(O) | Asn |
| 4-quinolylcarbonyl | Asn |
| Boc | βMeAsp |
| PhCH=CHC(O) | Asn |
| 3-isoquinolylcarbonyl | Asn |
| PhNHCH₂C(O) | Asn |
| Z | Asn |
| PhCH₂CH₂CH₂C(O) | Asn |
| 2-quinolylcarbonyl | βMeAsp |
| 2-quinolylcarbonyl | Thr |
| 1,2,3,4-tetrahydroisoquinol-3(R or S)-ylcarbonyl | Asn |
| (4-methoxy-2-quinolyl)carbonyl | Asn |
| 2-quinoxalinylcarbonyl | Thr |
| 2-quinolylcarbonyl | Tbg |
| CH₃C(O) | Val |
| 2-quinolylcarbonyl | Val |
| 2,3-dihydroindol-2(R or S)-ylcarbonyl | Asn |
| 2-quinoxalinylcarbonyl | Val |
| Z | Val |
| 2-quinolylcarbonyl | Asp-(cyPn) |
| Z | Tbg |
| 2-quinolylcarbonyl | Asn |
| 2-quinoxalinylcarbonyl | Asn |
| 2-quinolylcarbonyl | βCN-Ala |
| 6-quinolylcarbonyl | Asn |
| 3-quinolylcarbonyl | Asn |
| PhCH₂CH₂OC(O) | Asn |
| PhOCH₂C(O) | Thr |

(ii) a compound of formula 1 wherein the carbon atom bearing R¹ has the (R) configuration, X is 2-quinolylcarbonyl, R¹ is 1,1-dimethylethyl, R² and Q are each H, and A and Y are defined by one of the following combinations thereof:

| COMBINATION (A and Y) | |
| --- | --- |
| A | Y |
| Thr | (2,6-diisopropylphenyl)amino |
| Thr | (2,6-diethylphenyl)amino |
| Asn | NHCHPr₂ |

| COMBINATION (A and Y) | |
|---|---|
| A | Y |
| Asn | 1-isopropyl-2-methylpropylamino |
| Thr | (2,6-dimethylphenyl)amino |

(iii) a compound of formula 1 wherein $R^2$ and Q are each hydrogen and X, A, $R^1$ and Y are defined by one of the following combinations thereof, the compound being either a (R) or (S) diastereoisomer with respect to the asymmetric carbon atom bearing $R^1$:

| COMBINATION (X, A, $R^1$ and Y) | | | |
|---|---|---|---|
| X | A | $R^1$ | Y |
| Z | Asn | $(CH_3)_3C$ | $OCHEt_2$ |
| Z | Asn | $(CH_3)_2CH$ | $NHCHEt_2$ |
| Z | Asn | $(CH_3)_3C$ | $NHCHEt_2$ |
| 2-quinolylcarbonyl | Asn | $(CH_3)_2CH$ | $NHCHEt_2$ |
| Z | Val | $(CH_3)_3C$ | $NHCMe_3$ |
| 2-quinolylcarbonyl | Asn | $(CH_3)_3C$ | $NHCHEt_2$ |
| Z | Tbg | $(CH_3)_3C$ | $NHCHEt_2$ |

(iv) a compound of formula 1 wherein X is Z, A is Val, $R^1$ is H, $R^2$ is $(CH_3)_3CCH_2$, Q is H and Y is $NHCHEt_2$, the compound being either a (R) or (S) diastereoisomer with respect to the asymmetric carbon atom bearing $R^2$;

(v) a compound of formula 1 wherein X is Z, A is Val, $R^1$ and $R^2$ together with the carbon atoms to which they are attached form a 1,2-cyclohexanediyl, Q is H and Y is $NHCH_2CMe_3$, $NHCHPr_2$ or $NHCHEt_2$ the compound being a cis isomer with respect to the carbon atoms bearing $R^1$ and $R^2$;

(vi) 3(R)-tert-butyl-4-{2(R)-hydroxy-4-phenyl-3(S)-{[N-(2-quinolylcarbonyl)threonyl]-amino}butylamino}-4-oxobutyric acid isopropyl ester;

(vii) 3(R)-tert-butyl-4-{2(R)-hydroxy-4-phenyl- 3(S)-{[N-2-quinolylcarbonyl)asparaginyl]amino}butylamino}-4-oxobutyric acid 1-ethylpropyl ester;

(viii) $N^4$-{3(S)-{[N(benzyloxycarbonyl)-tert-butyl-glycyl]amino)-2(R)-hydroxy-4-phenylbutyl)-$N^1$-(1-ethylpropyl)-3(S)-tert-butylbutanediamide;

(ix) $N^4$-{3(S)-{[N(benzyloxycarbonyl)valyl]amino}-2(R)-hydroxy-4-phenylbutyl)-$N^1$-(1-ethylpropyl)-2 (R)-tert-butylbutanediamide;

(x) $N^1$(1-ethylpropyl)-$N^4$-{3(S)-{[N-(2-quinolylcarbonyl)threonyl]amino}-2(R)-hydroxy-4-(4-hydroxyphenyl)butyl)-3(R)-tert-butylbutanediamide;

(xi) $N^1$-(1-ethylpropyl)-$N^4$-{3(S)-{{(2,6-dimethylphenoxy)acetyl}-amino}-2(R)-hydroxy-4-(4-hydroxyphenyl)butyl)-3(R)-tert-butylbutanediamide;

(xii) a compound of formula 1 wherein the carbon atom bearing $R^1$ has the (R) configuration, A is absent, $R^1$ is tert-Bu, $R^2$ and Q each are hydrogen, Y is $NHCHEt_2$ and X is (1-methyl-2-indolyl)carbonyl, (4-chlorophenyl)carbonyl, (2,4-dichlorophenyl)carbonyl, (2,3,6-trichlorophenyl)carbonyl, (2-methylphenyl)carbonyl, (3-amino-2-methylphenyl)carbonyl, (2,4,6-trimethylphenoxy)acetyl or (2,6-dimethylphenoxy)acetyl; and (xiii) a compound of formula 1 wherein the carbon atom bearing $R^1$ has the (R) configuration, A is absent, $R^1$ is tert-Bu, $R^2$ and Q each are hydrogen, Y is (2,6-dimethylphenyl)amino and X is benzyloxycarbonyl, (2,6-dimethylphenoxy)acetyl or (2,5-dimethylphenyl)carbonyl.

8. A pharmaceutical composition comprising a compound as recited in claim 1, or a therapeutically acceptable acid addition salt thereof, and a pharmaceutically acceptable carrier.

9. A method for treating HIV infections in a human comprising administering thereto an effective amount of a compound as defined in claim 1, or a therapeutically acceptable acid addition salt thereof.

10. A method for protecting human cells against HIV pathogenesis comprising treating said cells with an anti-HIV effective amount of a compound as defined in claim 1, or a therapeutically acceptable acid addition salt thereof.

* * * * *